(12) United States Patent
Derr et al.

(10) Patent No.: US 8,100,533 B2
(45) Date of Patent: Jan. 24, 2012

(54) APPARATUS AND METHOD FOR SCREENING FOR GLAUCOMA USING VISUALLY EVOKED POTENTIALS

(75) Inventors: Peter H. Derr, East Windsor, NJ (US); Matt Emmer, Roslyn, NY (US)

(73) Assignee: Diopsys, Inc., Pine Brook, NJ (US)

( * ) Notice: Subject to any disclaimer, the term of this patent is extended or adjusted under 35 U.S.C. 154(b) by 0 days.

(21) Appl. No.: 12/435,678

(22) Filed: May 5, 2009

(65) Prior Publication Data

US 2010/0283973 A1 Nov. 11, 2010

(51) Int. Cl.
*A61B 3/02* (2006.01)
*A61B 3/00* (2006.01)
(52) U.S. Cl. ......... 351/239; 351/200; 351/222; 351/246
(58) Field of Classification Search ........... 351/239, 351/200, 205, 246, 221–222
See application file for complete search history.

(56) References Cited

U.S. PATENT DOCUMENTS

| | | | |
|---|---|---|---|
| 4,861,154 A * | 8/1989 | Sherwin et al. | 351/205 |
| 5,539,482 A | 7/1996 | James et al. | 351/246 |
| 6,477,407 B1 | 11/2002 | Klistorner et al. | 600/544 |
| 6,527,391 B1 | 3/2003 | Heiji et al. | 351/243 |
| 2003/0156255 A1 * | 8/2003 | Malov | 351/205 |
| 2009/0091706 A1 * | 4/2009 | Derr | 351/205 |

OTHER PUBLICATIONS

Haruki Abe, et al , Contrast Sensitivity and Pattern Visual Evoked Potential in Patients with Glaucoma, Documenta Ophthalmologica 65:65 70 (1987).

* cited by examiner

*Primary Examiner* — Dawayne A Pinkney
(74) *Attorney, Agent, or Firm* — Levisohn Berger LLP

(57) ABSTRACT

A pattern VEP system for screening for glaucoma and other optic nerve related diseases/deficiencies. The system combines high contrast and low contrast testing. The low contrast testing allows for highly sensitive glaucoma testing and the high contrast allows for a sensitive test of the central vision. The system also includes a narrowly tailored method of rejecting corrupted data allowing the system to selectively salvage useful portions of a signal. The system also provides a method of data modeling to locate the N75-P100-N135 complex in a waveform and determine if it falls within the normal range.

23 Claims, 9 Drawing Sheets

APPARATUS AND METHOD FOR SCREENING FOR GLAUCOMA USING VISUALLY EVOKED POTENTIALS

FIELD OF THE INVENTION

The current invention relates to the field of ocular testing, more specifically to an improved apparatus and method for screening for glaucoma and other diseases of the ocular or visual nervous system.

BACKGROUND OF THE INVENTION

Early detection of disease is of utmost importance in improving the odds of successful treatment. However, once a patient presents with disease symptoms, often, the disease is somewhat advanced or established. In order to truly discover a potential problem at earlier stages, asymptomatic patients should be screened for early signs of disease.

Glaucoma and other ocular and optic nerve-related diseases are among diseases that could potentially be detected at an early stage. There exists in the art a variety of tests that are capable of detecting early onset of glaucoma and other diseases of the optic nervous system. However, these tests are not suited as a screening tool to be used for the asymptomatic, general population.

For example, U.S. Pat. No. 6,527,391 to Heijl et al. is drawn to a typical method and apparatus for performing a computerized visual field test for identifying visual deficits. Such visual field tests typically are performed in one region of the eye at a time. They require long testing times and are compromised when a subject fixates on the wrong portion of a display. The recording of overt responses is also problematic in certain populations, including the preverbal, the non-verbal, the elderly and those who might intentionally or inadvertently hide their deficits.

U.S. Pat. No. 5,539,482 to James et al. is drawn to a glaucoma test using a pattern electroretinogram of a subject. In operation, the visual stimulus signals used are grating patterns, in contrast to a signal applied to individual eye zones modulated with a different temporal frequency. The use of an electroretinogram such as that proposed by James et al. for a glaucoma or vision test leads to a number of problems. An electroretinogram is highly problematic as it requires the attachment of an electrode to the cornea or sclera of a subject, who must thus have the eye locally anesthetized (and for children must be sedated) for the test. This limits the use of such a test to healthy populations, and demands that the test be performed in sterile environments such as hospitals. Moreover, known variations between subjects may cause the absolute comparison of any electroretinogram component to an "expected response component," as described by James et al., to be inaccurate or insufficiently sensitive. A still further problem is that the electroretinogram only identifies deficits in the retina, and not in all the various other regions of the visual tract, such as along the optic pathway or even in the brain.

U.S. Pat. No. 6,477,407 to Klistorner et al. is drawn to the use of a multifocal pattern visual evoked potential (mfVEP) for use in detecting visual field loss by comparing electrical brain activity acquired over two or more regions of the brain using very limited signal processing, e.g., the use of phase, frequency, and magnitude components, compared to each other and to corresponding display factors, are not disclosed.

The above-mentioned tests all require either lengthy testing times, local anesthetization of the eye (and for children must be sedated) or require for a patient to hold his/her eye still for the duration of testing. In addition, they produce results that are difficult to interpret. For these and other reasons, these prior art tests are not adapted for screening of non-symptomatic, healthy patients.

Pattern VEP is a well-known diagnostic aid in the detection of glaucoma and other optic nerve-related diseases. However, as practiced in the prior art, pattern VEP suffers from a lack of specificity, due to the fact that a distorted signal may be as a result a possible aberration on the lens of an otherwise healthy eye. The inability to distinguish between a healthy and diseased eye deems ordinary pattern VEP less than suitable as a screening device.

Additionally, prior VEP testing, to be effective requires skilled operators whose knowledge and experience may be required to interpret the results. This lessens the availability of such testing to large segments of the public because of the limited number of skilled operators and it may also introduce errors in the analysis because of the subjective nature of the tests.

Thus, there remains a need for an objective simplified, quick and non-intrusive screening test to detect early signs of ocular and optic nerve disease in asymptomatic patients.

SUMMARY OF THE INVENTION

The present invention is directed to a glaucoma screening test that utilizes Visually Evoked Potentials (VEP) derived from pattern reversals of low contrast and high contrast stimuli. The high contrast test ensures that a patient's central vision is healthy, specifically the parvocellular pathway, thereby eliminating the possibility that a distorted signal is incident to a lens aberration. The low contrast patterns activate the cells associated with the peripheral vision, specifically the magnocellular pathway. This contributes to increased sensitivity and specificity for glaucoma testing, which is a disease that often affects the peripheral magnocellular pathway at early onset.

The system also includes a novel system to salvage useful data. Specifically, if data is corrupted during the course of an event, the prior art systems conventionally rejects all data associated with that event. Rather than blindly rejecting data, the system of the present invention determines where the corruption occurs in the signal. If the corrupted data is in a signal area of no diagnostic importance, the portion of the signal containing the diagnostically important information will be salvaged. This correction for the under-inclusion of signals diminishes the need to run additional patterns, thereby shortening the duration of a test.

As each of a pre-determined number of successful signals are acquired during the course of a test, the system executes a signal averaging technique to signal average the most recently acquired signal with those acquired previously thereto. The resultant signal averaged waveform comprises the signal averaged data of each of the respective signals of each successful event of a particular test.

The system also executes a novel post-processing modeling operation on the resultant processed signal or waveform. The modeling operation determines whether or not such waveform falls within a normal range based on a number of parameters. The modeling essentially produces an optimized waveform to be compared to the measured waveform produced as a result of the test to determine if the measured waveform is significantly time delayed or comprises amplitudes below the optimized values, which signifies a possibility of ocular or optic nerve disease.

Thus, the current invention allows for the rapid objective screening of glaucoma in asymptomatic patients, which produces easy-to-interpret results, and it is therefore adapted for widespread use.

DETAILED DESCRIPTION OF THE INVENTION

Figure 1:
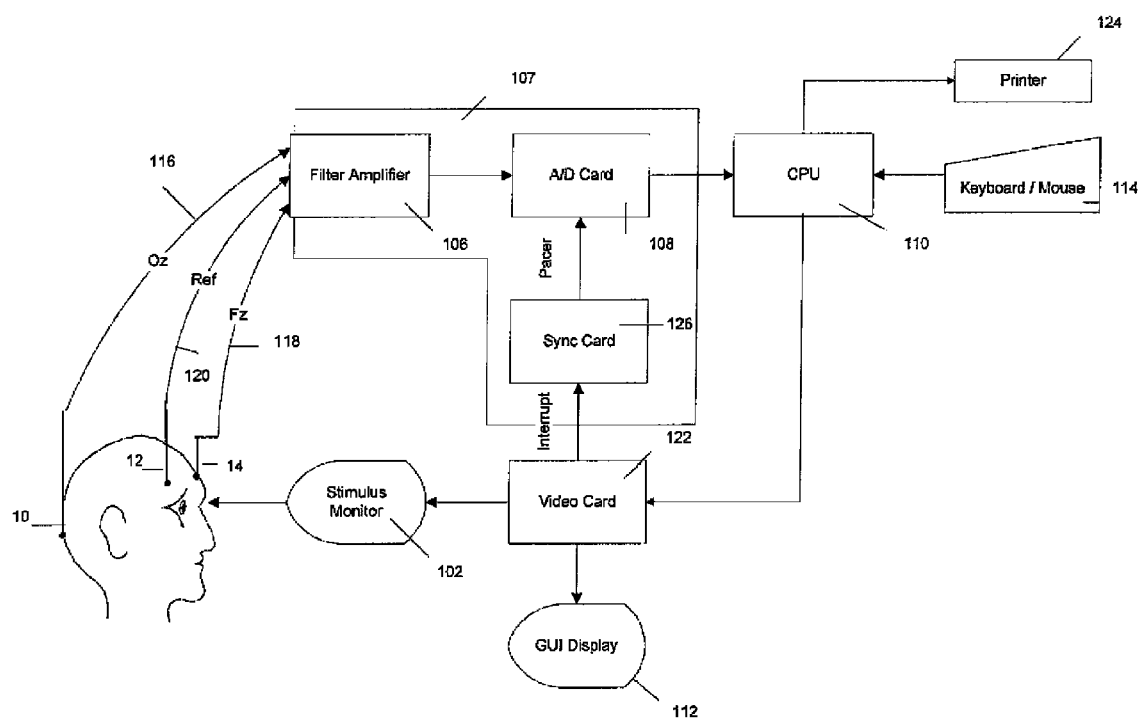
FIG. 1 is a block diagram of a system interface according to an embodiment of the invention.

Embodiments of the present invention will now be described with reference to the above-identified Drawings. However, the Drawings and the description herein of the invention are not intended to limit the scope of the invention. It will be understood that various modifications of the present description of the invention are possible without departing from the spirit of the invention. Also, features described herein may be omitted, additional features may be included, and/or features described herein may be combined in a manner different from the specific combinations recited herein, all without departing from the spirit of the invention.

As earlier described, the disclosed invention utilizes pattern Visually Evoked Potentials to screen patients for ocular deficienies. VEPs are caused by a sensory stimulation of a subject's visual pathway and are detected by electrodes placed on a subject's scalp. One advantage of the use of VEP testing is that a test subject does not need to give an overt or verbal response to a stimulus, as the VEP is naturally and unconsciously produced during vision. This not only allows testing of the young, the old, the infirm, those who have language impairments, and those whose language differs from that of the doctor or tester, but also avoids false information from the subject, who for any number of reasons may wish to conceal a visual impairment. A further advantage is that the VEP represents the visual response as initiated in the eye and carried to the visual cortex. Accordingly, the VEP captures impairments at any point or structure along this pathway, thereby determining the likelihood of more possible impairments than a mere eye exam can.

In diagnosing/screening patients using VEP, the N75-P100-N135 complex conveys important information about the condition of the retina's ganglion cells and optic nerve generating and transmitting the evoked action potential. The N75-P100-N135 complex, which is well know in the art of VEP, corresponds roughly to the depolarization and repolarization phases of an action potential. Latency or diminished amplitudes of the N75-P100-N135 response may indicate nerve damage such as loss of conduction, for example, due to a myelin sheath deficiency. It is thus, the N75-P100-N135 complex that is the focus of VEP testing. Signal portions that are not associated with the N75-P100-N135 complex are, for the most part, diagnostically uninteresting.

Pattern VEP, in particular, is superior to multifocal VEP for screening purposes. That is because with multifocal VEP, patterns change around the periphery of a subject's visual field in order to test the same. However, the eye has a tendency to track movement, and therefore, the test is easily compromised as it is difficult for a patient to keep his/her eye perfectly still during the course of multifocal testing. Multifocal testing, therefore, requires a system to ensure the steadiness of a subject's eye, it requires much longer testing times, especially when eye movement is detected and it is not well suited for children.

Figure 2:
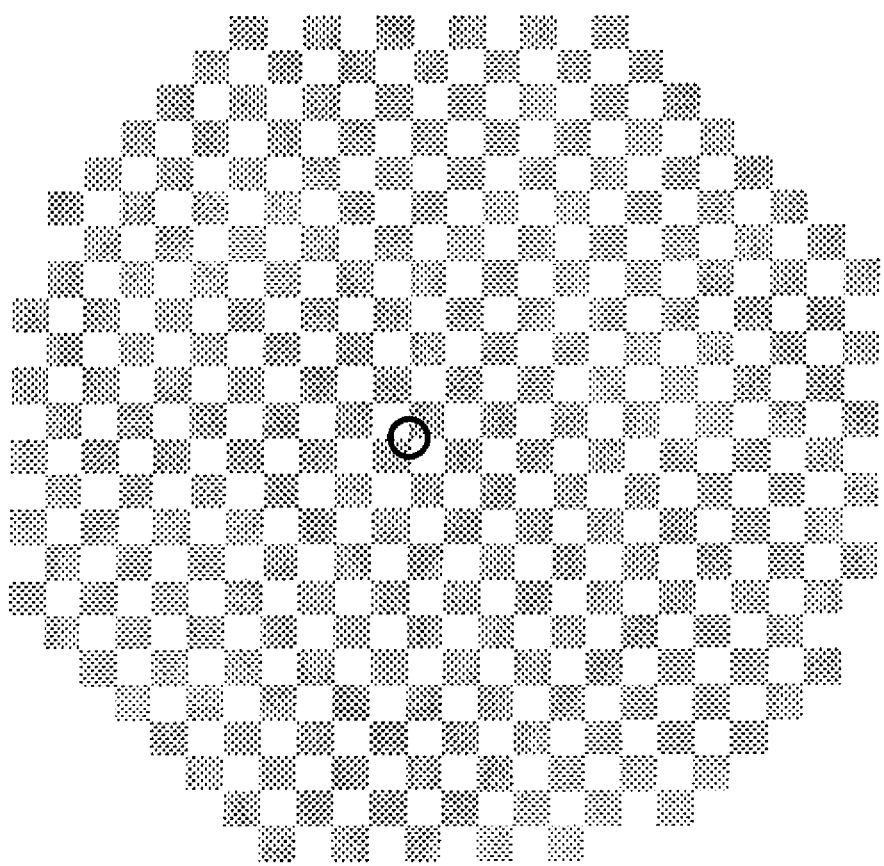
FIG. 2 shows a low contrast, checkerboard pattern that is utilized in an embodiment of the invention.

In one preferred embodiment of the current invention, a low contrast scan is performed on each eye individually and then on both eyes together, repeated thereafter with a high contrast scan. In the low contrast scan, a pattern, such as the checkerboard pattern shown in FIG. 2, is displayed on a display device and observed by a viewer. The pattern is then successively reversed, such that black boxes turn white and vice versa. In a preferred embodiment, the low contrast patterns comprise a contrast of roughly 5-20%. More preferably the contrast is in the range of 8-12%. In one preferred embodiment, 10% contrast is utilized. Low contrast patterns bias toward cells of the magnocellular pathway, and they are therefore well suited for the detection of early glaucoma. It will be understood by one of ordinary skill in the art that patterns may comprise concentric circles or a variety of other shapes.

Figure 3:
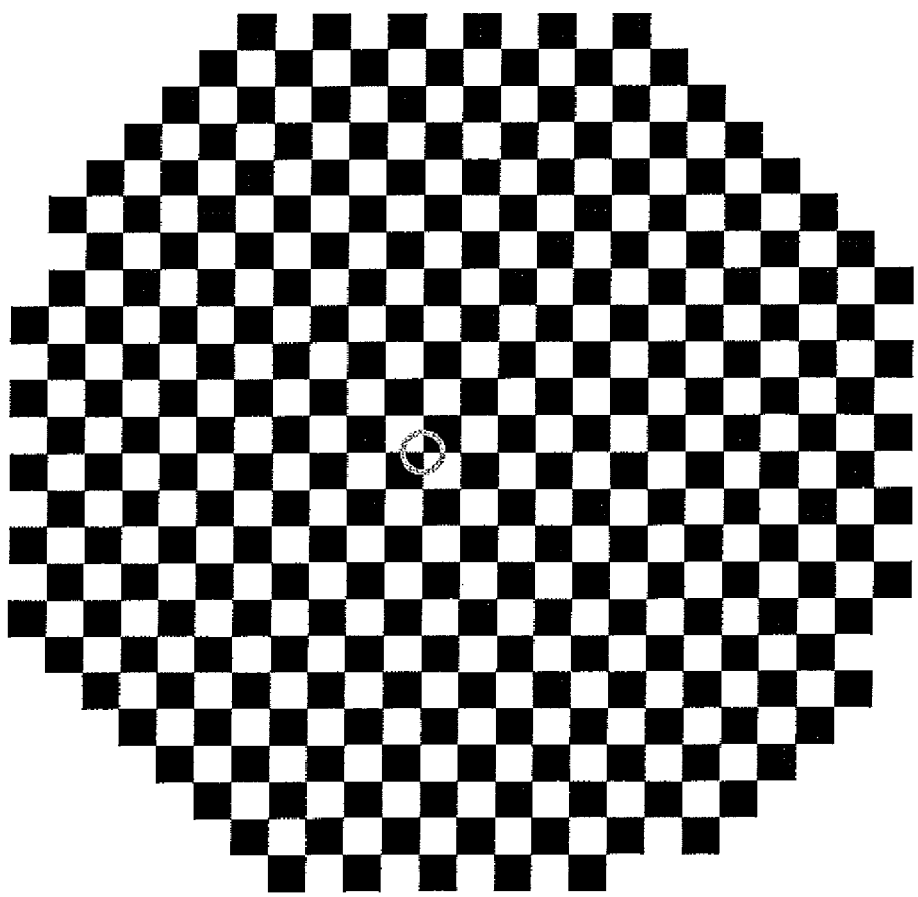
FIG. 3 shows a high contrast, checkerboard pattern that is utilized in an embodiment of the invention.

High contrast patterns, as shown in FIG. 3, are preferably in the range of 70-85% contrast; more preferably, the range is 80-85%. In one preferred embodiment, an 85% contrast is utilized. High contrast patterns bias toward cells of the parvocellular pathway, and they are therefore suited to test a patient's central vision. The preferred contrast ranges described above will excite the parvocellular cells without saturating the same. The high contrast component of the test ensures that a patient's central vision is in the healthy range. Therefore, if a distorted signal is produced in the low contrast portion of the test, there is increased likelihood that a distortion is due to nerve damage and not due to an abnormality of the lens of a patient (e.g. refractive error, cataract) with a healthy optic nerve system. This combination of low contrast and high contrast VEP testing has not been taught or suggested in the prior art. More importantly, running high contrast patterns as an exclusionary measure to rule out lens abnormalities has not been taught, disclosed or otherwise suggested in the prior art.

In a preferred embodiment, a stimulus-generating device is programmed to reverse patterns roughly every 500 milliseconds. One of ordinary skill in the art would recognize that the rate of pattern reversal could be other than 500 ms and is preferably between 300 and 1000 ms. For the purposes of this application, it will be assumed that patterns are reversed every 500 milliseconds.

Each time a pattern is reversed (or flipped), a VEP is generated, which is captured and converted into an electrical signal. Each pattern flip and a signal acquired in response thereto is referred to as an "event" herein. A "successful event" herein refers to a pattern flip for which an acquired signal, or a portion thereof, is selected by the program to be used diagnostically. An "unsuccessful event" refers to a pattern flip for which a resultant signal is rejected by the system and is not used diagnostically. As will be further explained below, a signal that is corrupted in an area of diagnostic importance will be rejected by the system.

In a preferred embodiment, each test comprises 40 successful events. That is, the test will be deemed to be complete after the system has acquired 40 successful events or 40 signals that are deemed to be diagnostically useable. Assuming a pattern reversal rate of 500 ms, the shortest time it would take to achieve 40 successful events is 20 seconds. If during the course of testing, the system encounters unsuccessful events it will continue running patterns until 40 successful events are attained. One of ordinary skill in the art would recognize that a test, which is based on more or fewer than 40 successful events, could be implemented and is within the scope of the current invention.

Referring to FIG. 1, a system configuration of the hardware components according to an embodiment of the invention is shown. As shown, a display device 102, or stimulus monitor is provided for displaying patterns to a viewer 104. Sensors 10, 12 and 14, such as disposable electrodes, attached non-invasively to a patient's scalp detect responses of the visual pathway to stimuli. Such responses are amplified, digitized, recorded and analyzed by a data acquisition system. Conductors 116, 118 and 120 collect information from sensors 10, 14 and 12 respectively, which are positioned on the scalp of the patient 104 over the visual cortex, the frontal cortex, and the parietal cortex, respectively. Conductors 116, 118 and 120 are connected to data acquisition system 107.

The VEP data acquisition system 107, which acquires responses to brain stimuli, comprises an instrumentation amplifier and filter 106, an analog to digital converter (A/D) 108 and a synchronization system such as a synchronization card 126. The amplifier 106 receives VEP signals from conductors 116, 118 and 120 and amplifies and filters the same. Such amplified signals are then supplied to an analog to digital converter 108 for converting the analog VEP signals into digital form. The data acquisition system 107 is connected to a central processing unit 110 of a computer for controlling the operations and functions of the VEP recording and measuring device. The CPU is connected to a visual stimulus generating device such as a video card 122, which has outputs connected to a Graphic User Interface (GUI) or monitor 112, to the stimulus monitor 102, and through a synchronization card 126 to the data acquisition system 107. The GUI 112 displays data captured by the VEP data acquisition system and conveys information concerning the operation of a test being conducted to an operator. Keyboard/Mouse 114, connected to CPU 110, allows for an operator to input information to the computer relating to a subject being tested. A printer 124 also connected to the CPU allows for test results to be printed. The above referenced video card 122 is controlled by the CPU to generate the patterns that are perceived by the patient on monitor 102. The above referenced synchronization card 126, synchronizes the periodic visual stimulus and the sampling rate for recording the VEP signal responses.

The computer used to control operations, execute routines and store data may comprise at least one or more processors and memory storage devices. The computer also may receive a number of inputs and outputs for communicating information externally.

The computer operates under the control of an operating system and software applications, components and programs that execute the routines and systems described herein. In general, the routines executed to implement the embodiments of the invention, whether implemented as part of an operating system or a specific application, component, program, object, module or sequence of instructions will be referred to herein as "the system", or "software".

Those skilled in the art will recognize that the exemplary hardware structure illustrated in FIG. 1 is not intended to limit the present invention. Indeed, those skilled in the art will recognize that other alternative hardware and/or software environments may be used without departing from the scope of the invention.

Figure 4:
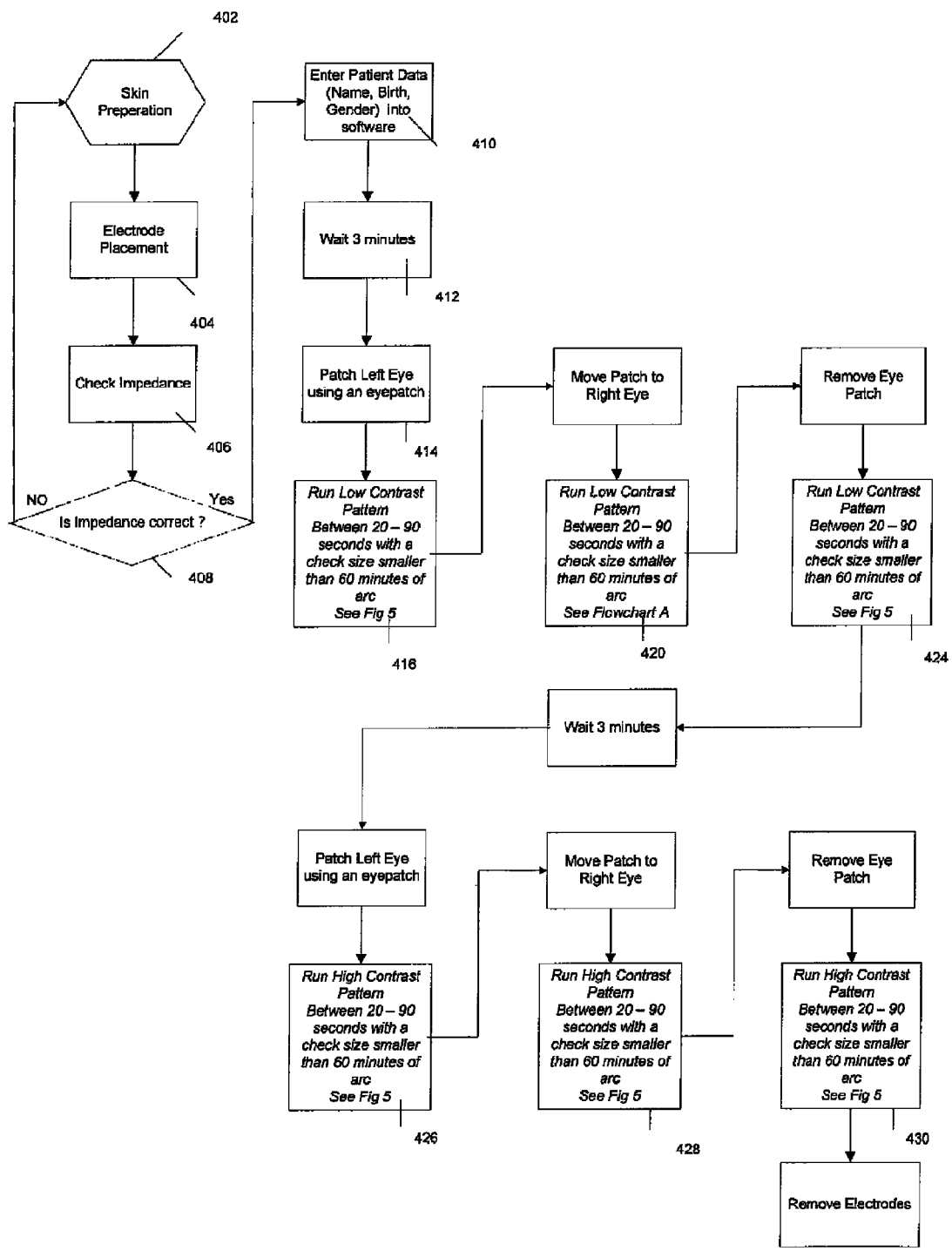
FIG. 4 is a flow chart of a system for performing a VEP test according to an embodiment of the invention.

FIG. 4 is a flow chart, of the order of testing operations, according to an embodiment of the invention. The operations are performed on the system of FIG. 1. At initial step 402, a patient's skin is prepared for receiving electrodes. The electrodes, or sensors 10, 12 and 14, are then placed on a patient's scalp 404, and the impedance is checked 406. If the impedance is correct 408, a test operator enters the patient's data into the system 410 through keyboard 114. After waiting approximately three minutes 412, one eye is patched 414, readying the unpatched eye for testing.

Preferably, the low contrast scan is run first, with the high contrast scan following thereafter, but it will be understood that the order of testing described herein could be reversed or alternated.

Figure 5:
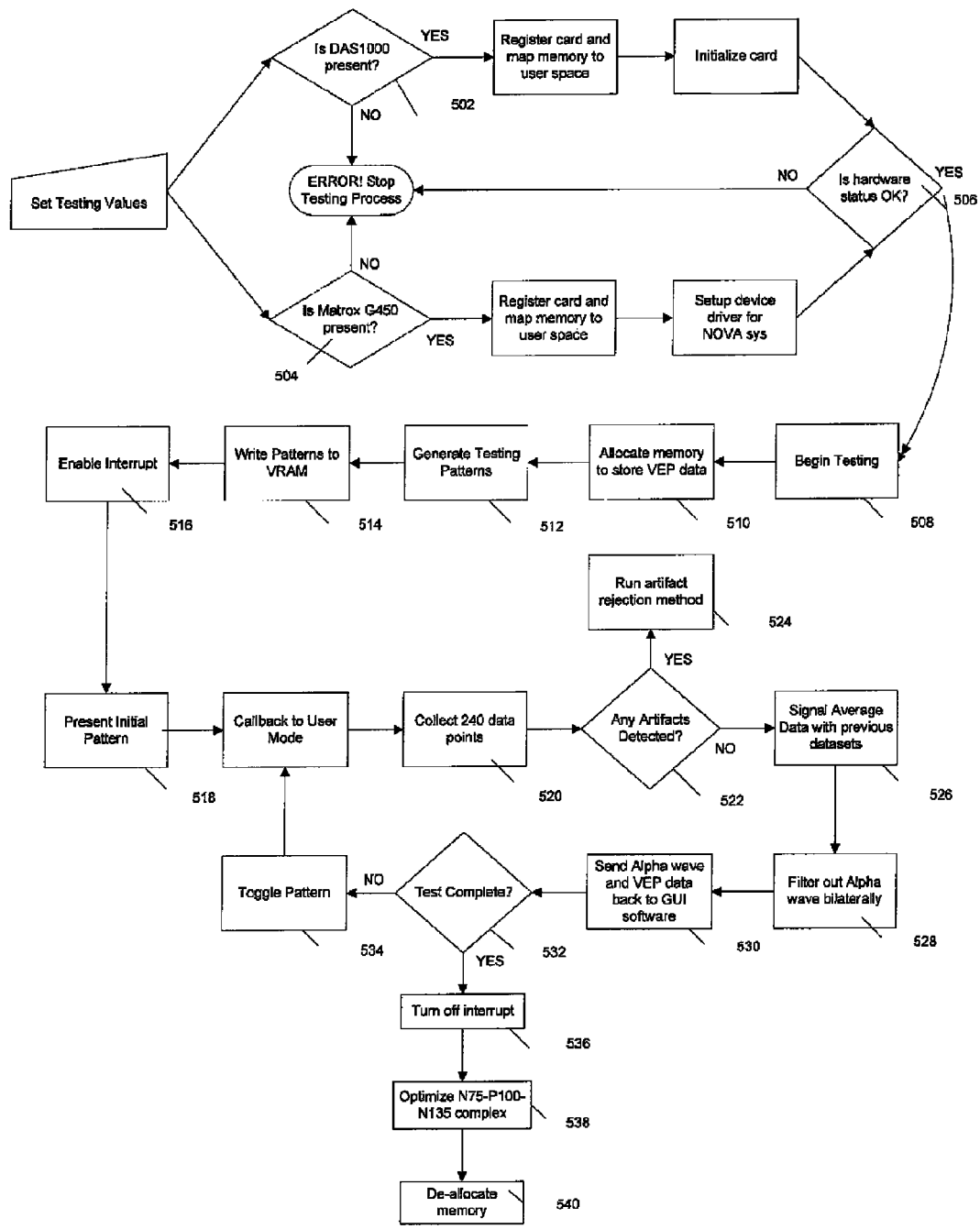
FIG. 5 is a flow chart showing some of the steps performed for each pattern reversal in the flow chart of FIG. 4.

At step 416, with one eye patched, a patient gazes at the display device 102, which begins running a low contrast test For each test (i.e. series of 40 successful events), the system executes an operation as illustrated in the flow chart of FIG. 5.

Referring to FIG. 5, at initiation, the software, under control of CPU 110, is programmed to run a check of the A/D card 502 (108 of FIG. 1) and video card 504 (122 of FIG. 1). After confirming proper hardware function 506, 508, the system allocates memory to store VEP data that is about to be acquired 510. The software then begins to run successive test patterns 512, which are written to the VRAM 514 of the video card 122. At step 516, the system enables the interrupt system. The interrupt system synchronizes the temporally modulated visual stimulus with the sampling ("pacer") clock of the A/D for recording the VEP signal responses, which allows for the rapid and accurate acquisition of desired responses. The interrupt system uses the vertical blank interrupt of stimulus monitor 102 (FIG. 1) as the synchronized time base for flipping the VEP stimulus pattern between two phase shifted patterns (one being the inverse of the other) at a specified temporal frequency. In addition, the interrupt routine phase locks data acquisition of the analog to digital card 108 to the pattern flipping temporal frequency. Without this level of synchronization, extraneous noise would be induced into the system and latency information of the N75-P100-N135 complex would be incorrect U.S. Pat. No. 6,475,162 describes the interrupt system in greater detail as incorporated by reference in its entirety herein.

After enabling the interrupt system, the first pattern is then presented on the stimulus monitor 518 (102 of FIG. 1) and a VEP is generated. For each event, the software is programmed to collect 240 data points 520. After each pattern is displayed and a signal is acquired, the system checks the recently acquired signal to determine a presence of any artifact 522. If an artifact (corrupted data) is detected in an area of diagnostic importance, the recently acquired data will be rejected 524 and the software will add an additional flip to make up for the one that was rejected. If no artifacts are detected, the system performs a signaling averaging routine 526, to signal average the newest acquired signal with those that were acquired previously thereto.

In one embodiment of the invention, the system filters out alpha waves 528 and sends them to the CPU 530 to alert the test operator to the fact that a subject may not be properly focusing on the patterns.

The system then checks to see if the test is complete 532 by determining whether or not a predetermined number of successful events have been recorded. If the predetermined number of successful event has not been attained, the system generates another pattern(s) 534 until a predetermined number of successful events are achieved. Once the requisite number of successful events is attained, the interrupt system and visual stimulus is terminated 536, the VEP data is filter averaged 538 and memory is de-allocated 540.

After completing the low contrast scan on a first eye, the second eye is then tested with low contrast patterns. Referring back to FIG. 4, after the right eye has been tested with low contrast patterns, a patch is removed from the left eye and placed on the right eye 418 to prepare the left eye for testing. At step 420 testing of the left eye is initiated. As described above, the system will perform the routine of FIG. 5, this time for the left eye. Thereafter, a test is run on both eyes 424, once again performing the routine of FIG. 5. At steps 426, 428 and 430, the above is repeated, this time using high contrast patterns.

As described, often, during the course of recording VEP responses, data could be corrupted. For example, if a patient blinks or suddenly moves, a significant amount of noise can be introduced into a signal. Typically, due to the sensitivity of the electrodes, such noise will saturate the data acquisition system. Any such saturation is deemed to be a corrupted signal (corrupted data).

As noted above, prior art systems search for any corrupted data that may have been introduced during an event. If such corrupted data is found, the entire event will be rejected and will not be utilized for diagnostic purposes. Because the diagnostically important information lies in the region of a signal that corresponds to the N75-P100-N135 complex, data corruption that occurs outside thereof is of no consequence. Yet, the prior art systems blindly reject all data in which a corruption was detected, even though the diagnostically important part of the signal may be uncorrupted. This leads to the unnecessary rejection of diagnostically important data. As a result, additional stimulus iterations are necessary to achieve a requisite number of successful events. This may add significant time to the duration of a VEP test.

The inventive system comprises a novel system for selectively rejecting data only if a corruption occurred in a signal portion corresponding to the N75-P100-N135 complex. If a corruption occurs in a signal area of no diagnostic importance—i.e. in an area outside of the N75-P100-N135 complex, the signal is salvaged and utilized. This limits the number of extra stimulus iterations to those that are diagnostically unusable, and consequently allows for faster VEP testing.

In the broadest sense, if an event, or stimulus lasts for a time period "P", the prior systems examine a signal corresponding to "P" and rejects the entire signal if corruption is detected. The current system achieves greater efficiency by examining a signal portion that corresponds to less than "P". This allows for a rejection system that is narrowly tailored to reject only data that is truly unusable.

Figure 6:
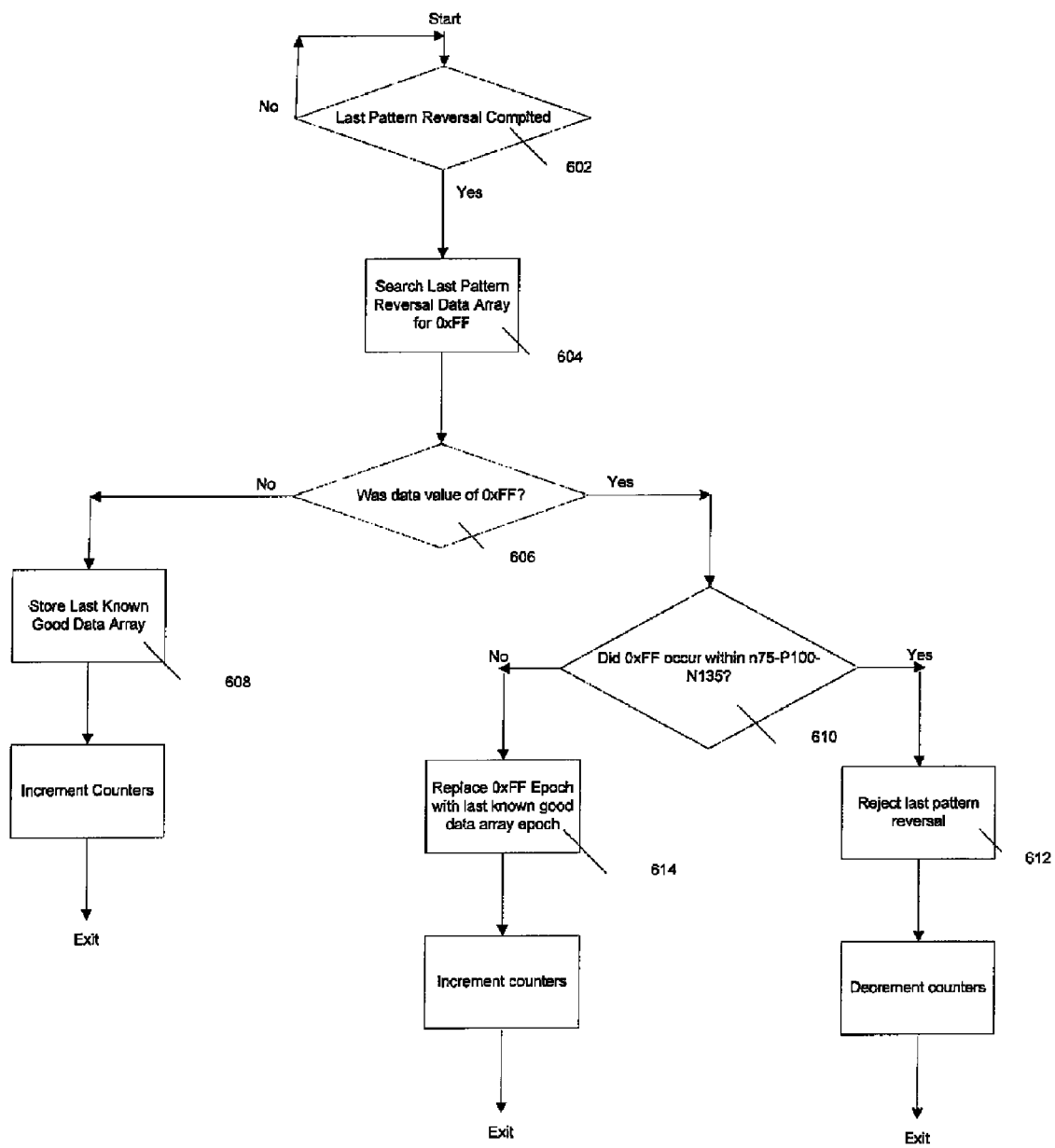
FIG. 6 is a flow chart of a system for rejecting corrupted data according to an embodiment of the invention.

FIG. 6 is a flow chart of the artifact rejection system of the invention. After each event (pattern reversal and acquired response) 602, the system searches the data array acquired in that event for any signal saturation 604 and determines whether or not any such saturation has occurred 606. If no signal saturation was found, the recently acquired data array is stored in memory 608 and is utilized for diagnostic purposes.

On the other hand, if the system detects data saturation at step 606, it executes further operations to determine whether or not the corruption occurred within the N75-P100-N135 complex 610. To this end, the system searches only a specific window of time, during which the N75-P100-N135 complex is expected to occur (the N75-P100-N135 search window). If the corruption is found within that window, then the event is rejected 612. If the corruption is not found within the N75-P100-N135 search window, it is deemed immaterial and the data array is kept 614.

In a preferred embodiment the N75-P100-N135 search window is roughly from 70-140 ms after the initiation of an event. The window could be extended from 70-200 ms after initiation of an event. In one preferred embodiment, the window is the first 400 milliseconds after initiation of a stimulus. The expanded window will capture extremely latent signals, for example, in patients with advanced glaucoma.

It should be noted that the artifact rejection routine of FIG. 6 is preferably, initiated while a pattern is displayed and stimulus is ongoing. For example, assuming a pattern reversal rate of 500 ms, and a N75-P100-N135 search window of 400 ms, although the visual stimulus lasts for 500 milliseconds, the search window is limited to the first 400 millisecond of stimulus. Therefore, the artifact search is initiated when 400 ms of stimulus is reached. As such, during the first 400 ms of a pattern display, the system acquires data. In the last 100 ms the artifact rejection routine is run.

In another embodiment at step 604 only an N75-P100-N135 window is searched for a presence of data corruption. If no saturation is detected, the signal is utilized. If saturation is detected, the signal is rejected. Note that the terms "saturation" "corruption" and "artifact" are used interchangeably to refer to a data array that contains corrupted data.

Figure 7:
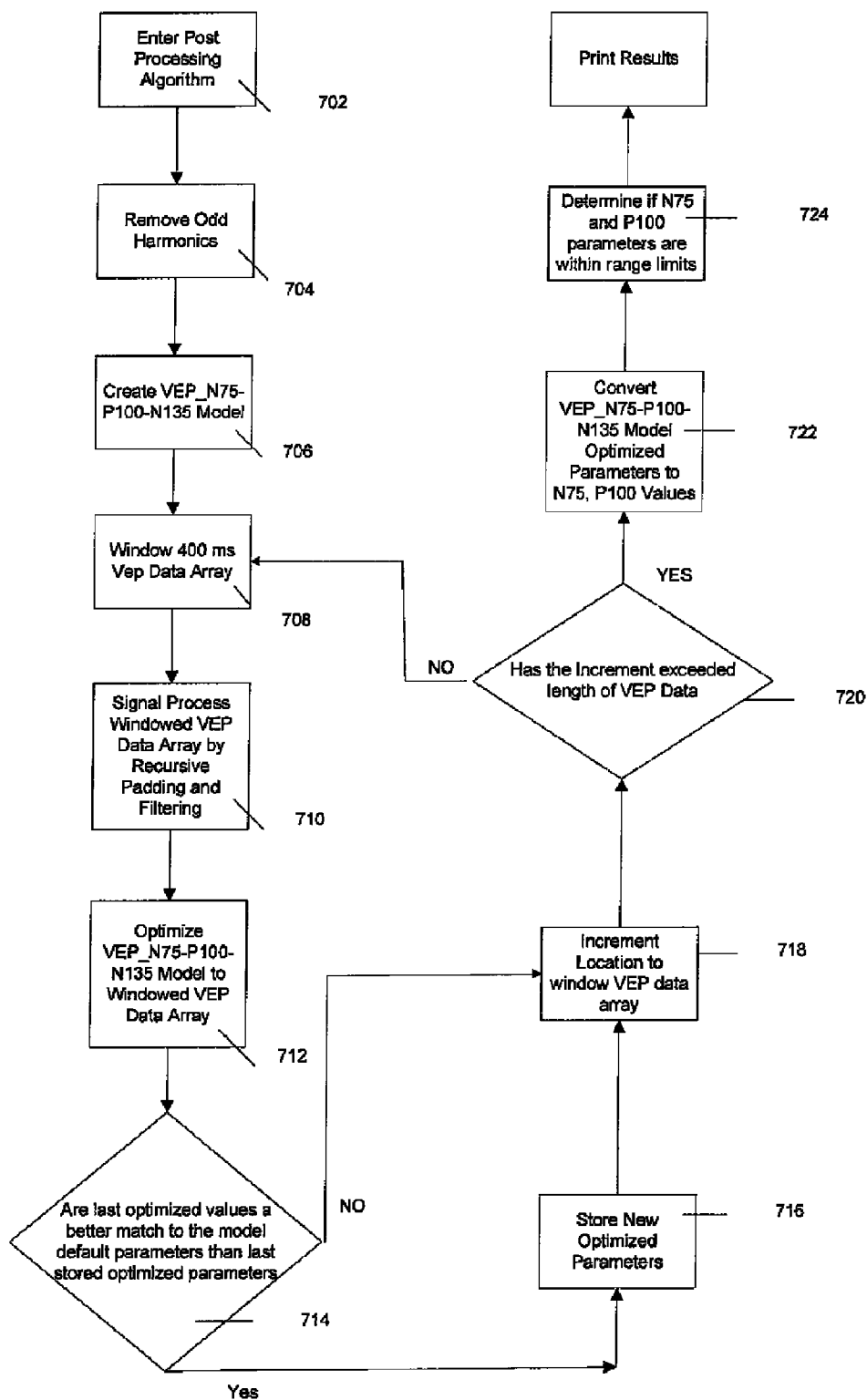
FIG. 7 is a flow chart of a glaucoma processing system using data modeling according to an embodiment of the invention.

As previously mentioned, the inventive system provides a novel data modeling system to determine whether or not a resultant waveform is within a normal or desired range. Referring to FIG. 7, after a predetermined number of successful events have been recorded, which were successively signal averaged by the system, through software running on the CPU, to produce a time sequenced average signal (acquired signal). The system then executes post-processing operations 702 on the acquired signal. Odd harmonics are removed 704 to eliminate noise from the signal. Thereafter, the system applies a preliminary model structure or waveform 706 with which to compare the recently acquired signal, for example by way of a signal comparator running on the CPU. The system defines a window 708 comprising the first 400 milliseconds of a 500 ms stimulus within which to locate the optimized N75-P100-N135 complex. It is noted that the N75-P100-N135 complex—even assuming some amount of latency—will typically occur within the first 200 ms of an event. However, in one embodiment the current system provides an extended window, and searches data that corresponds to the first 400 ms after a stimulus 708. In this manner, the system can be used to analyze signals from patients with advanced ocular and optic nerve disease, whose resultant signal may be skewed drastically to the right due to latency.

Figure 9:
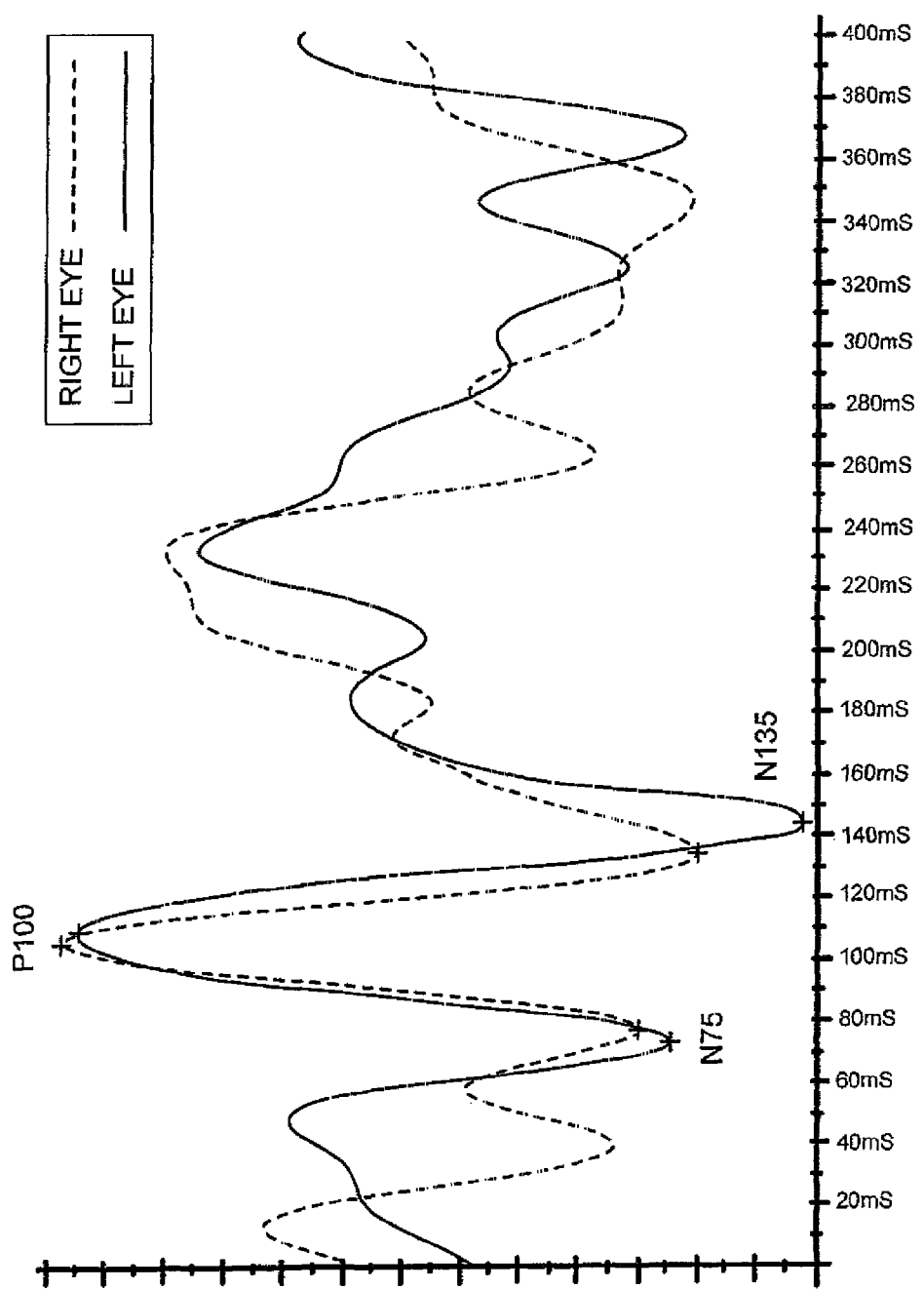
FIG. 9 shows two processed resultant signals from a test of a patient's right and left eyes according to an embodiment of the invention.

Beginning at $T_{0\ ms}$, the system will incrementally move across an acquired signal (as shown in FIG. 9) until $T_{400\ ms}$. At selected increments, the system will compare the newly acquired signal to the model signal, searching for sets of data points on the acquired signal to compare that signal to the model signal in seeking such data like the location of the N75-P100-N135 complex and signal amplitude that can be optimized to a number of parameters on the model structure 712. At each increment, the system will search for optimized data points within a narrow search window.

At each increment, as each new window is created the acquired signal could be further processed, for example, by recursive padding and filtering 710 to further remove spurious and other undesirable signal components.

In a preferred embodiment, this optimization is accomplished by applying the double envelope model as defined by the following formula to an acquired signal to extract certain parameter values:

$$M(t) = A1^*(t/tc1\, e^{(1-t/tc1)})^{N1} {}^* \mathrm{Sin}(2\pi F1\, t/100 + ANG1^*\pi/180) + \\ A2^*(t/tc2\, e^{(1-t/tc2)})^{N2} {}^* \mathrm{Sin}(2\pi F2\, t/100 + ANG2^*\pi/180)$$

Where:
A1=Envelope 1 Amplitude
TC1=Envelope 1 Center Frequency
N1=Exponential Decay Rate
F1=Frequency of Envelope 1
ANG1=Phase Angle of Envelope 1
A2=Envelope 2 Amplitude
TC2=Envelope 2 Center Frequency
N2=Exponential Decay Rate
F2=Frequency of Envelope 1
ANG2=Phase Angle of Envelope 2

Preferably, the optimization method is set with two tolerance settings and a maximum number of iterations. The first tolerance is the model's individual parameter tolerance, meaning that once a parameter value when trying to continue to optimize does not change by more than the specified tolerance (i.e., 1%) that parameter is considered preliminarily optimized. The method will move on to the next parameter to optimize. The second tolerance is the model's optimization criteria. This means that once the model matches the VEP data by this tolerance (i.e. 1%) the model is considered optimized. The number of iterations setting sets a threshold for attempting to optimize the specified VEP data. If the number of iterations times out the next set of VEP data will be attempted to be optimized As can be seen if a model poorly matches the VEP data tight tolerances optimization will never be achieved.

After each comparison between the model structure and the acquired signal is made, the system determines if the most recent match is a better match than previously compared data points 714. If the most recent match is, in fact, a better match than a previous one, the newest optimized parameters are updated and stored 716. If after step 714, the system does not determine that a current match is better than a previous one, the next increment is examined 718. If the entire window has not been examined, at step 720, the system repeats the process until an entire window of a predetermined length of time has been examined for a best comparison to a model structure or waveform.

Once a full window has been examined, the system compares the optimized structure with that of the default model structure 722. The system then determines if the optimized structure is within a normal range 724.

The present methods and apparatuses are for determining the "likelihood" of a visual deficit in a subject. This terminology is used to clarify that, while these methods and apparatus may in some cases be capable of diagnosing the presence of a specific visual deficit, they are more often capable of, or configured to, merely screen for the likelihood of a visual deficit of one or more kinds. This "likelihood" may be in the form of a binary determination ("yes" or "no") or may optionally report a numerical measure of probability ("10% likely"), although other determinations may also be made. For example, the system could be programmed to analyze a resultant waveform according to a number of parameters, and then generate a "yes" (i e. follow-up warranted) or a "no" (i.e. no follow-up warranted) based on the level optimization of a resultant signal to a model waveform. Alternatively, the computer could generate a numerical measure of the level of optimization of a resultant signal to a model waveform.

Figure 8:
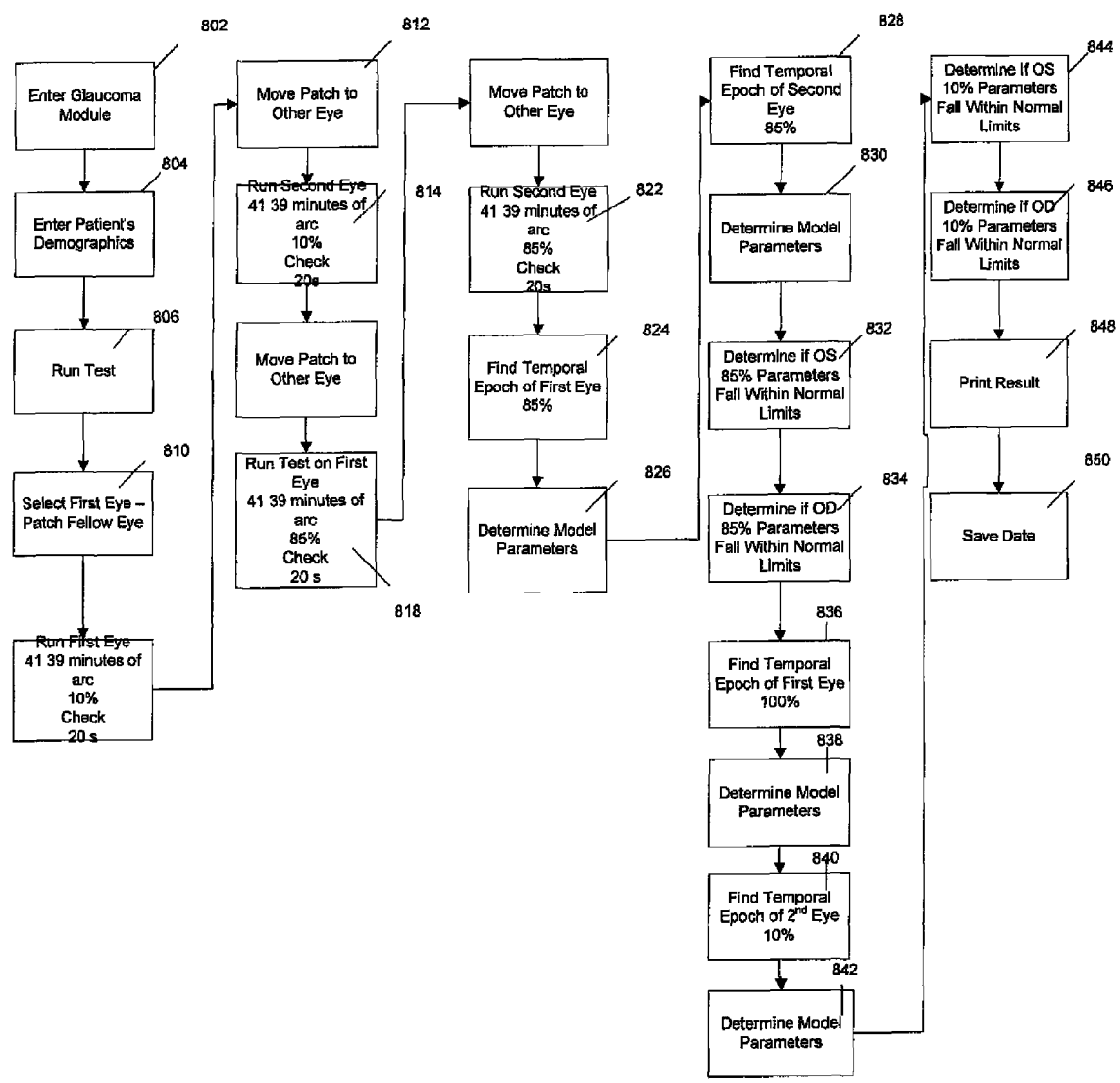
FIG. 8 is a flow chart of the testing and processing steps executed during the course of a test according to an embodiment of the invention.

FIG. 8 is a flow chart showing an overview of a glaucoma screening test. At initiation of the glaucoma module 802, the system will prompt an operator to input patient information 804. The system then runs a test 806 to make sure that all hardware/software components are working properly prior to initiating a test. A patch is applied to one eye of a patient, readying the other eye for testing 808. (Note that each time one eye is tested, the untested eye is patched. The steps of alternating the patch between eyes will not be mentioned). Thereafter, the system begins displaying patterns having a 10% contrast on the stimulus monitor. After achieving a predetermined number of successful events, the patient's second eye is tested with low contrast patterns 814. After testing each of the eyes with low contrast patterns, the high contrast pattern test is initiated, as before, beginning with a first eye 818 and then moving to a second eye 822.

Having acquired and stored a signal averaged data array for each test, the system then executes further data processing and analysis. Beginning with the signal acquired from the high contrast test of one eye, the system locates the N75-P100-N 135 complex 824 and compares it to a model waveform 826. Thereafter, the system locates the N75-P100-N135 complex from the high contrast test of the second eye 828 and compares it to model parameters 830. The system then determines whether or not the signal acquired for the first eye 832 and second eye 834 are each within normal limits. The system then repeats the process on the signal averaged data from the low contrast test. As before the N75-P100-N135 complex is located 836 and compared to a model waveform 838 for each of the eyes tested 836-842. The system then determines whether or not the signals acquired via low contrast testing for each of the eyes fall within the normal range—based on a plurality of parameters 844, 846. The system then prints the results and additionally stores them on a memory device connected to the CPU 850.

In a preferred embodiment, a high contrast and low contrast test is run on both eyes simultaneously (not shown in FIG. 8). In an embodiment, such data is collected and stored for future reference only.

The present disclosure is drawn to methods and an apparatus for quickly and automatically screening visual deficits/ocular deficiencies in a subject with a minimum of expertise required by testing staff. The term "visual deficit" refers not only to deficiencies, defects, injuries, or impairments in one or both of a subject's eyes, but also to deficiencies, defects, injuries, or impairments along the entire visual pathway. The present disclosure can determine the likelihood of a deficits not only in the structural elements of an eye (cornea, anterior chamber, posterior chamber, vitreous humor, lens, fovea, macula, etc.), but also in the optic nerve, optic chiasm, optic tract, LGN, geniculostriate pathway, and visual cortex, in communication with one or both eyes. The likelihood of a number of known illnesses, disorders, and diseases may be determined using the disclosed methods, including (but not limited to) glaucoma; macular degeneration; macular dystrophy; retinitis pigmentosa; Laurence-Moon-Bardet-Biedl syndrome; Stargardt's disease; inflammation of the retina; inflammation of the choroid; Serpiginous Choroiditis; cortical blindness; cataracts; basic refractive problems; strabismus; and combinations thereof.

Having described this invention with regard to specific embodiments, it is to be understood that the description is not meant as a limitation since further modifications and variations may be apparent or may suggest themselves to those skilled in the art. It is intended that the present application cover all such modifications and variation as fall within the scope of the appended claims.

What is claimed is:

1. A method of screening for ocular deficiency in a patient, comprising the steps of:
    displaying a plurality of successive high contrast patterns on a display device;
    detecting visually evoked potentials (VEP) generated from said patient observing said high contrast patterns;
    generating a plurality of signals from said VEPs of said patient observing said high contrast patterns;
    signal averaging said plurality of signals to yield a signal averaged waveform, said signal averaged waveform comprising an N75-P100-N135 complex:
    identifying said N75-P100-N135 complex in said signal averaged waveform:
    comparing parameters of said N75-P100-N135 complex to model parameters;
    displaying a plurality of successive low contrast patterns on a display device;
    detecting VEPs generated from said patient observing said low contrast patterns;
    generating a plurality of signals from said VEPs of said patient observing said low contrast pattern;
    signal averaging said plurality of signals to yield a signal averaged waveform, said signal averaged waveform comprising an N75-P100-N135 complex;
    identifying said N75-P100-N135 complex in said signal averaged waveform:
    comparing parameters of said N75-P100-N135 complex to model parameters; and
    determining a likelihood of a visual defect based on said comparison of said signal averaged waveform produced by said low contrast patterns to model parameters and based on said comparison of said signal averaged waveform produced by said high contrast patterns to model parameters.

2. The method of claim 1, further comprising the step of screening for central vision deficiencies.

3. The method of claim 1, wherein said high contrast is in a range of between approximately 70-85%.

4. The method of claim 1, wherein said high contrast is in a range of between 80-85%.

5. The method of claim 1, wherein said low contrast is in a range of approximately 5-20%.

6. The method of claim 5, wherein said low contrast range is between 8-12%.

7. The method of claim 1, wherein said high contrast and low contrast patterns are checkerboard patterns.

8. An apparatus for screening of ocular deficiency in a patient, comprising:
    means to generate a plurality of successive high contrast patterns said high contrast patterns being in a range of between approximately 70-85%;
    means to display said plurality of successive high contrast patterns;
    sensors applied to the scalp of said patient, said sensors detecting visually evoked potentials (VEP) generated from said patient observing said high contrast patterns;
    means to generate a signal from said VEP of said patient observing said high contrast patterns;
    means to signal average a plurality of signals generated by said patient observing said high contrast patterns to produce a signal averaged waveform;
    means to compare said signal averaged waveform to model parameters;
    means to generate a plurality of successive low contrast patterns said low contrast patterns being in a range of between approximately 5-20%;
    means to display said plurality of successive low contrast patterns;
    said sensors detecting VEPs generated from said patient observing said low contrast patterns;
    means to generate a signal from said VEP of said patient observing said low contrast pattern;
    means to signal average a plurality of signals generated by said patient observing said low contrast patterns to produce a signal averaged waveform;
    means to compare said signal averaged waveform to model parameters;
    signal comparing means to compare said signal averaged waveform produced by VEPs generated from said high contrast patterns to model parameters and to compare said signal averaged waveform produced by VEPs generated by said low contrast patterns to model parameters to screen for a likelihood of ocular deficiencies.

9. A method of screening for ocular deficiency in a patient, comprising the steps of:
    displaying a pattern on a display device;
    reversing said pattern displayed on said display device, each reversal occurring after said pattern was displayed for a given time period;
    detecting a visually evoked potentials (VEP) generated from said patient observing said pattern for said time period;
    generating a signal from said VEP of said patient observing said pattern;
    detecting signal saturation in said signal, said detecting step comprising searching for an occurrence of signal saturation, said searching conducted during a search window of time that is less than said given time period;
    rejecting said signal event if said signal saturation occurred within said window that is less than said given time period; and
    processing said signal if signal saturation occurs outside said window.

10. The method of claim 9, wherein said search window is 200 ms.

11. The method of claim 9, wherein said search window is 100 ms.

12. The method of claim 9, wherein said search window corresponds to between 70 and 140 milliseconds after an initiation of a pattern.

13. The method of claim 9, further comprising the steps of
    displaying a plurality of patterns to said patient and processing a plurality of signals generated by said plurality of patterns,
    signal averaging each of said signals with all prior generated respective signals to produce a waveform reflecting said test,
    said waveform generated after a predetermined number of non-rejected signals; and
    and comparing said waveform with a model waveform.

14. The method of claim 13, further comprising the step of producing a final pass/fail indication for the screening test.

15. The method of claim 13, wherein said predetermined number is approximately 40.

16. The method of claim 13, wherein said search window comprises the N75-P100-N135 complex in said respective processed signal.

17. Apparatus for screening for ocular deficiency of a patient, comprising
- pattern generation means connected to a display to display said pattern to be viewed by said patient;
- means to reverse said pattern, said reversed pattern being displayed on said display for a given period of time;
- sensors applied to the scalp of said patient, said sensors detecting visually evoked potentials (VEP) generated from said patient observing said pattern;
- means to generate a signal from said VEP of said patient observing said pattern;
- means to detect signal corruption in said signal comprising searching for occurrences of signal corruption, control means to conduct said search conducted during a search window of time that is less than said given time period;
- rejecting said signal if said signal corruption occurred within said window that is less than said given time period; and
- permitting said event to be processed if signal corruption occurs outside said window.

18. The apparatus of claim 17, wherein said search window is corresponds to 200 ms of said signal.

19. The apparatus of claim 17, wherein said search window corresponds to 100 ms of said signal.

20. The apparatus of claim 17, wherein said search window begins at a time corresponding to 70 ms after the start of a signal.

21. The apparatus of claim 17, further comprising
- means to process a plurality of signals generated by VEPs of said patient observing a plurality of patterns,
- the processing of the signal for each said plurality of patterns generating a respective signal,
- means to signal average each of said respective signals with all prior generated respective signals to produce a waveform reflecting said test,
- said waveform generated after a predetermined number of non-rejected signals;
- and means to compare said waveform with a model waveform.

22. The apparatus of claim 21, comprising a means to produce a final pass/fail indication for the screening test.

23. The apparatus of claim 21, wherein said search window comprises the N75-P100-N135 complex in said respective processed signal.

* * * * *